United States Patent [19]

Jennings, Jr.

[11] 3,991,110

[45] Nov. 9, 1976

[54] PREPARATION OF HEXAMETHYLPHOSPHORAMIDE

[75] Inventor: Hamlet Grey Jennings, Jr., Richmond, Va.

[73] Assignee: E. I. Du Pont de Nemours and Company, Wilmington, Del.

[22] Filed: Dec. 29, 1972

[21] Appl. No.: 319,896

[52] U.S. Cl. .............................. 260/551 P
[51] Int. Cl.² ................................. C07F 9/22
[58] Field of Search .................. 260/551 P, 551

[56] References Cited
UNITED STATES PATENTS

| | | | |
|---|---|---|---|
| 2,487,859 | 11/1949 | Dickey et al. | 260/551 |
| 2,662,095 | 12/1953 | Isham | 260/551 |
| 3,084,190 | 4/1963 | Miller et al. | 260/551 |

OTHER PUBLICATIONS

Parker Adv. Organic Synthesis, vol. 5 pp. 22–23 (1965).
Normant, Angew Chem., Internat. Ed., vol. 6, pp. 1046–1067 (1967).
Kirby et al., The Organic Chemistry of Phosphorus, pp. 274–277,301,304–306,325–327 (1967).

*Primary Examiner*—John D. Randolph

[57] ABSTRACT

An improved process for preparing hexamethylphosphoramide by reacting phosphorus oxychloride and dimethylamine in a liquid diluent, the improvement comprising employing hexamethylphosphoramide as the liquid diluent.

4 Claims, 1 Drawing Figure

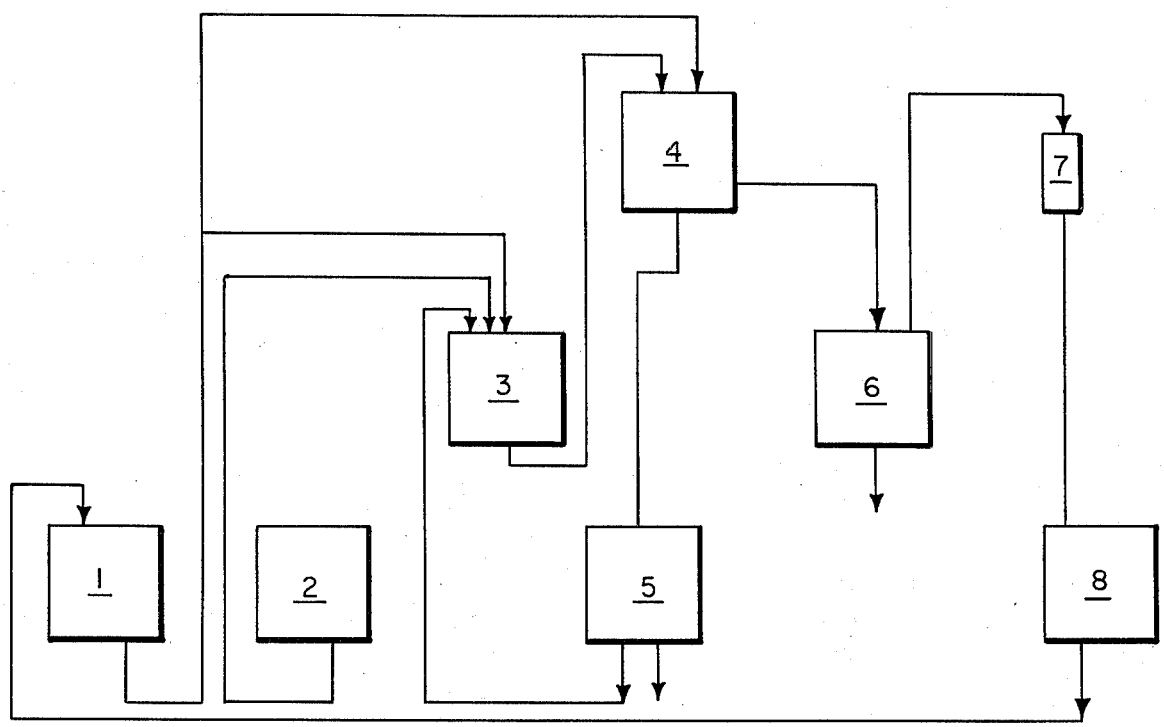

PREPARATION OF HEXAMETHYLPHOSPHORAMIDE

BACKGROUND OF THE INVENTION

1. Field of the Invention

This invention relates to a process for preparing hexamethylphosphoramide.

2. Description of the Prior Art

Hexamethylphosphoramide is a well known compound having a variety of utilities, for example, as a solvent in polyacrylonitrile spinning operations and in processes for removing acetylene from gas streams. It is commonly prepared by reacting phosphorus oxychloride and an excess of dimethylamine in an inert organic solvent. Upon completion of the reaction the by-product dimethylamine hydrochloride is filtered off and the hexamethylphosphoramide, dimethylamine and organic solvent are separated by distillation. Inert organic solvents which are useful in such a reaction include chloroform, ethers, such as dipropyl ether and dibutyl ether, and aromatic and substituted aromatic compounds, such as benzene, ethyl benzene and xylene. Such prior art processes may provide difficulties due to the poor filterability of the by-product dimethylamine hydrochloride. Moreover, since the hexamethylphosphoramide is soluble in the organic solvent, isolation of the desired product requires separation thereof from the solvent. Representative prior art processes for the preparation of hexamethylphosphoramide are included in U.S. Pat. Nos. 2,662,095 and 3,084,190.

SUMMARY OF THE INVENTION

It is an object of this invention to provide an improved process for preparing hexamethylphosphoramide. A further object is to provide such a process wherein the hexamethylphosphoramide is recovered in aqueous brine.

The present invention resides in an improved process for preparing hexamethylphosphoramide by reacting phosphorus oxychloride and dimethylamine in a liquid diluent, the improvement comprising employing hexamethylphosphoramide as the liquid diluent.

DETAILED DESCRIPTION OF THE INVENTION

Although hexamethylphosphoramide is known to react with phosphorus oxychloride, in the improved process of this invention the former proves to be a useful liquid diluent even though phosphorus oxychloride is a reactant and hexamethylphosphoramide is the desired product of the reaction. By employing hexamethylphosphoramide as a liquid diluent in the process described herein, the dimethylamine hydrochloride by-product is formed as readily filterable crystals.

In practice, about 2 parts of dimethylamine are mixed with about 3 parts of hexamethylphosphoramide and about 1 part of phosphorus oxychloride is then added gradually, all parts being by weight. About 95% of the phosphorus oxychloride is converted to hexamethylphosphoramide. Generally, the amount of dimethylamine should be at least 20% in excess of the stoichiometric amount calculated to react with the phosphorus oxychloride. Although dimethylamine aids in maintaining fluidity of the reaction mixture, a large excess thereof merely increases the load on recovery facilities. The amount of hexamethylphosphoramide should be at least twice the amount of phosphorus oxychloride, on a weight basis, so that the dimethylamine hydrochloride slurry which is produced can be agitated efficiently and handled readily. The reaction generally is carried out at 0°–40° C., preferably at about 20° C. The dimethylamine, which has a low atmospheric pressure boiling point (7.4° C.) is retained in the reaction vessel either by means of a reflux condenser or by operating at superatmospheric pressure. Although the hexamethylphosphoramide is known to react with phosphorus oxychloride, the excess dimethylamine minimizes this side reaction and the hexamethylphosphoramide product is readily obtained in 95% yield by the process of this invention.

The reaction between dimethylamine and phosphorus oxychloride is very rapid and exothermic. Heat of reaction is removed by a cooling jacket or coil in the reaction vessel, or by an external heat exchanger. After all of the phosphorus oxychloride has been added, the charge can be heated to 40°–45° C. to ensure completion of the reaction. The dimethylamine hydrochloride by-product is insoluble in the reaction mixture and, unless a relatively large volume of hexamethylphosphoramide is employed as the reaction medium, the mixture can become quite thick and difficult to stir. The difficulty can be avoided by circulating the reaction mixture through an exterior filter or centrifuge, thereby removing the insoluble hydrochloride salt as it is formed, and returning the clear liquid to the reaction vessel. In either case, the mixture is filtered and the liquid filtrate is collected, as product or for return to the reaction vessel as the liquid diluent for a subsequent run.

The wet hydrochloride filter cake or centrifuge cake may contain about 30–50 wt. % of hexamethylphosphoramide. In a preferred process, the wet cake is mixed with water to dissolve the hydrochloride. To dissolve 100 parts of dimethylamine hydrochloride, about 80 parts of water are employed. The aqueous mixture containing hexamethylphosphoramide and dissolved dimethylamine hydrochloride is then made basic, for example, with caustic soda, to free the dimethylamine and form an inorganic salt, for example, sodium chloride. Dimethylamine is removed by distillation, leaving a residual aqueous solution containing about 10–20 wt. % of hexamethylphosphoramide, 10–20 wt. % of inorganic salt, for example, sodium chloride, and a small amount of caustic soda, dimethylamine and organic byproducts. The aqueous solution of hexamethylphosphoramide can be conveniently handled and transferred in this form.

In another procedure for carrying out the latter part of this preferred embodiment, the wet cake containing hexamethylphosphoramide is washed with dimethylamine, dissolving out the hexamethylphosphoramide and leaving behind dimethylamine hydrochloride wet with dimethylamine. The hydrochloride is dissolved in water, the solution is made basic and the dimethylamine is recovered therefrom by distillation. The solution of dimethylamine and hexamethylphosphoramide can be returned to the reaction vessel (after analysis) for use in a subsequent charge. The amount of dimethylamine present in the solution determines the amount of phosphorus oxychloride added to the charge for the next batch.

The process of the invention can be operated either as a continuous or semi-continuous process or as a batch process of the type just described. Using the reaction vessel as a one stage continuous reactor, hexamethylphosphoramide, dimethylamine and phosphorus oxychloride can be fed simultaneously at a ratio of approximately 3:2:1 while the reaction mixture containing essentially no phosphorus oxychloride is removed at the same rate. Continuous filtration can be employed to remove dimethylamine hydrochloride which is wet with hexamethylphosphoramide; the wet cake can be continuously dissolved and neutralized in a vessel feeding a continuous still. Distillation removes dimethylamine at the top of the column while a solution of hexamethylphosphoramide in aqueous brine is removed at the bottom. The chemical reactions can be carried out in pipelines rather than in vessels, if desired. Hexamethylphosphoramide can be isolated by extraction from the aqueous brine with an ether, followed by fractional distillation.

BRIEF DESCRIPTION OF THE DRAWING

The FIGURE shown in the drawing is a block diagram representing apparatus employed in carrying out the improved process of this invention.

Referring now to the FIGURE shown in the drawing, 1 represents a storage tank for dimethylamine and 2 represents a tank for storing phosphorus oxychloride. Phosphorus oxychloride can be fed to dimethylamine in reactor 3 which is an agitated vessel from which the slurry, after completion of the reaction, can be fed to the filter system 4 which represents a combined filter system and temporary storage for the filter cake containing dimethylamine hydrochloride and hexamethylphosphoramide. The filter system represented by 4 can comprise a centrifuge or other means for separating liquid hexamethylphosphoramide from a filter cake containing hexamethylphosphoramide and solid dimethylamine hydrochloride. 5 Represents a tank for storing hexamethylphosphoramide liquid product. From 5 the product can be removed for shipment or for use in another process, or it can be returned to reactor 3 for use as liquid diluent in a subsequent run. 6 Represents a still for distillative recovery of dimethylamine from aqueous alkaline brine. 7 Represents a condenser in the dimethylamine distillation system and 8 represents a receiver tank for storage of distilled dimethylamine which can be transferred to dimethylamine storage tank 1.

EXAMPLE 1

This example utilized a jacketed, 2 liter, reaction vessel having a bottom outlet; brine or hot water was circulated through the jacket. The reactor was equipped with an agitator, a brine cooled condenser, a dropping funnel and an entry for introducing dry nitrogen. A line led from the bottom outlet to the top of a flask which was equipped with an agitator, a sintered glass filter plate above its bottom outlet and means for providing suction thereto. To the nitrogen purged reaction vessel were added 675 grams of hexamethylphosphoramide and 485 grams of dimethylamine, the temperature being maintained at about 20° C. From the dropping funnel through a leg extending below the surface of the solution in the reactor were added 230 grams of phosphorus oxychloride in about 2.5 hours; the temperature was maintained at 0°–25° C. When the phosphorus oxychloride addition was complete, the charge was heated to 40°–45° C. for one hour; the excess dimethylamine was maintained in the reaction vessel by means of a reflux condenser. The charge was then transferred to the filter flask, cooled to 20°–25° C. and the dimethylamine hydrochloride and hexamethylphosphoramide were separated by filtration. About 685 grams of hexamethylphosphoramide were obtained (filtrate).

The filter cake, containing about 365 grams of dimethylamine hydrochloride and 245 grams of hexamethylphosphoramide, was dissolved in 300 grams of water and transferred to a still. To the charge in the still were added 500 grams of 30% aqueous caustic soda. The dimethylamine was then distilled until the pot temperature reached 110° C., or the temperature at the top of the distillation column reached 20° C. The product in the still was hexamethylphosphoramide in aqueous brine; concentration was about 16% hexamethylphosphoramide.

EXAMPLE 2

The reaction vessel (same as used in Example 1) was purged with dry nitrogen, then charged with 473.7 grams (450 ml.) of hexamethylphosphoramide and 306 grams (450 ml.) of dimethylamine. With the temperature maintained at 20°–25° C., 96.6 grams (46 ml.) of phosphorus oxychloride were added gradually. After all of the phosphorus oxychloride had been added, the charge was stirred at 20°–25° C. for an additional 0.5 hour. The charge was filtered on a Buchner funnel through No. 1 Whatman filter paper, leaving a filter cake of dimethylamine hydrochloride wet with hexamethylphosphoramide. The hexamethylphosphoramide filtrate was returned to the reaction vessel. The filter cake was washed twice with 136 grams (200 ml.) of dimethylamine, the washings being added to the hexamethylphosphoramide in the reaction vessel. After a waiting period of several days, 96.6 grams (46 ml.) of phosphorus oxychloride were gradually added at 20°–25° C. as before and the slurry was filtered and isolated and the cake was washed twice with 136 grams of dimethylamine. The combined washings weighed 267 grams and were returned to the reaction vessel as part of the makeup for the following charge. A portion of the good quality product filtrate hexamethylphosphoramide was returned to the reaction vessel to provide a total of 474 grams of hexamethylphosphoramide when added to the amount contained in the wash filtrates.

I claim:

1. Improved process for preparing hexamethylphosphoramide by reacting phosphorus oxychloride and dimethylamine in a liquid diluent, the improvement comprising reacting the phosphorus oxychloride and dimethylamine, at 0°–40° C., in the presence of hexamethylphosphoramide, the amount of dimethylamine being at least 20% in excess of the stoichiometric amount calculated to react with the phosphorus oxychloride, the amount of hexamethylphosphoramide being at least twice the amount, on a weight basis, of the phosphorus oxychloride.

2. The process of claim 1 wherein the amount of dimethylamine is at least twice the amount, on a weight basis, of the phosphorus oxychloride and the amount of hexamethylphosphoramide is at least three times the amount, on a weight basis, of the phosphorus oxychloride.

3. The process of claim 1 wherein the hexamethylphosphoramide diluent and the dimethylamine are first admixed and the phosphorus oxychloride is added to the mixture.

4. The process of claim 1 wherein part of the hexamethylphosphoramide produced is recycled as diluent and part is recovered in aqueous brine.

* * * * *